United States Patent [19]

Edwards

[11] 4,058,897
[45] Nov. 22, 1977

[54] AMALGAM RETRIEVER

[76] Inventor: Frank E. Edwards, 5937 Birchwood Drive, Great Bend, Kans. 67530

[21] Appl. No.: 713,184

[22] Filed: Aug. 10, 1976

[51] Int. Cl.² ............................................. A61C 17/00
[52] U.S. Cl. .................................... 32/40 R; 210/522; 210/157
[58] Field of Search ................ 210/522; 209/157, 155, 209/156, 459; 32/33, 40 R, 40 A

[56] References Cited

U.S. PATENT DOCUMENTS

| | | | |
|---|---|---|---|
| 1,935,461 | 11/1933 | Unkie et al. | 209/157 |
| 3,703,467 | 11/1972 | Lummus et al. | 210/522 |
| 3,777,403 | 12/1973 | Ritchie | 32/33 |

Primary Examiner—Robert Peshock
Attorney, Agent, or Firm—Cushman, Darby & Cushman

[57] ABSTRACT

A device is shown for use in a dental office or the like where particles of precious metal or amalgam are to be recovered from a flushing stream. The construction utilizes a housing for enclosing a downwardly sloping trough element through which a flushing liquid flows so that the particles of metal or amalgam can deposit in compartments formed in the trough while the flushing liquid and any residual debris which floats in the liquid flows through an outlet to a sewage disposal means.

11 Claims, 3 Drawing Figures

AMALGAM RETRIEVER

BACKGROUND OF THE INVENTION

In the dental art, it is known to recover amalgam and heavier metal particles flowing in a stream formed of flushing liquid and debris by passing the liquid stream through relatively complicated sump structures, as shown in the U.S. patents to Mitchell, U.S. Pat. No. 3,305,927, issued Feb. 28, 1967; Ritche, U.S. Pat. No. 3,777,403, issued Dec. 11, 1973; and Ritzler, 3,870,483, issued Mar. 11, 1975. These devices are designed to receive the liquid stream of flushing water and the usual mixture of debris from the dentists' activities, including washing water, tartar scraped from the teeth, tooth particles, cotton and gauze fibers, blood clots, buffing compounds, ground off tooth swarf, broken fillings, including particles of amalgam, saliva and other debris removed from the mouth during the performance of dental work on a patient. While such known sump structure may serve more or less efficiently to separate amalgam from a flow of flushing liquid, they cannot be easily disassembled for cleaning and sterilization when it is necessary to recover the accumulated amalgam and to prepare the sump for further use.

A device making use of a riffle structure for the recovery of precious metal from the flow in natural streams is illustrated in the U.S. Patent to Craft et al, No. 2,926,786, issued Mar. 1, 1960. Such a device, while embodied in a relatively simple structure, does not provide a means that can be sterilized or easily adapted to wholly contain a waste flow from a dental operation. The open sluice-type structure, shown in this patent, is not intended to wholly contain a fluid flow containing matrial to be separated from the flow, and thus would not provide a sterile device adapted for use in a confined space, such as a dentist's office or the like.

BRIEF DESCRIPTION OF THIS INVENTION

The structure of the present invention includes a fully enclosed riffle flow trough-like element over which a stream of liquid is directed to flow at a velocity which permits heavier metal particles to be deposited out of the flow while agitation resulting from the stream flow over the baffles causes debris from dental activities to remain suspended in the flushing flow and to be discharged from the lower end of the trough. The device can be assembled by telescoping a trough element into and sealing it in a transparent tubular housing and holding the assembled device in this condition by passing a single tie bolt from an inlet end cap to an outlet end cap. This simplified structure provides for easy assembly and disassembly of relatively few parts from which the amalgam may be recovered, and which parts may thereafter be cleaned and, where necessary, sterilized before reassembly.

It is therefore an object of this invention to provide a device for the efficient recovery of particles of amalgam and precious metals.

Another object of this invention is to provide a simplified structure for use in a dentist's office that may be quickly assembled and disassembled for cleaning and sterilization.

Another object of this invention is to provide such a structure fabricated of a minimum number of parts requiring sterilization.

A still further object of this invention is to provide a structure having a minimum number of crevices therein that need be cleaned and sterilized after use.

Other objects will appear from the detailed description below.

IN THE DRAWINGS

DETAILED DESCRIPTION

Figure 1:
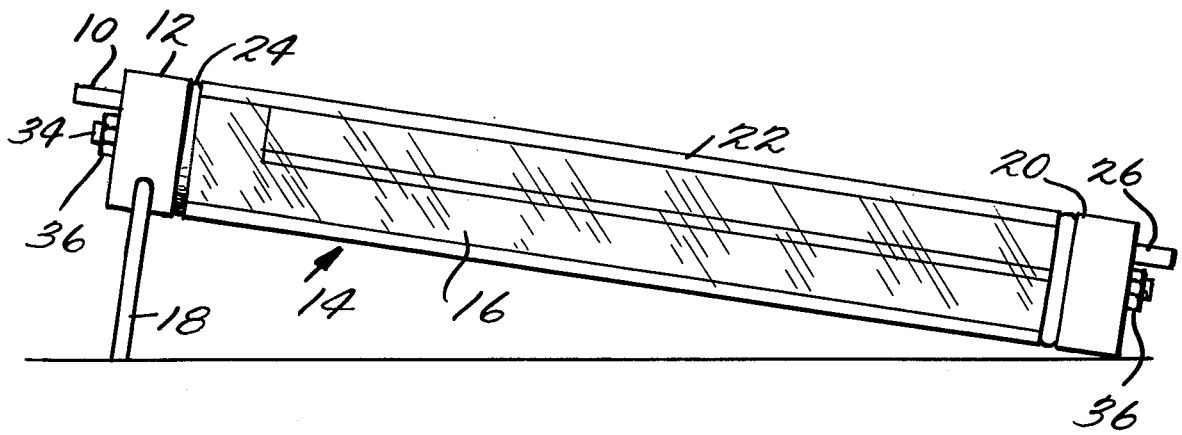
FIG. 1 is a side elevation showing the assembly of the amalgam recovery device.
Figure 2:
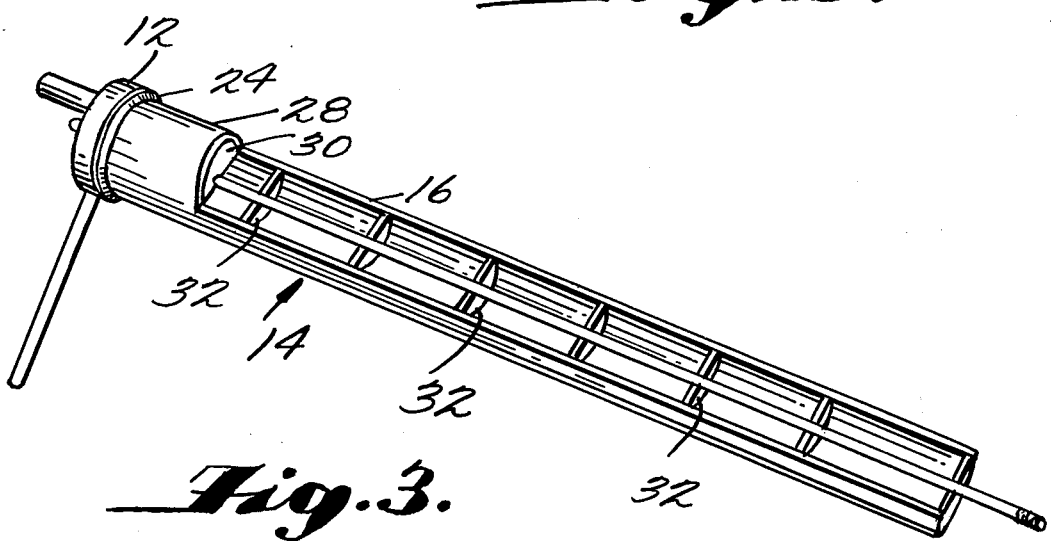
FIG. 2 is a perspective view of the trough element of the device shown in FIG. 1, with the glass housing removed.
Figure 3:
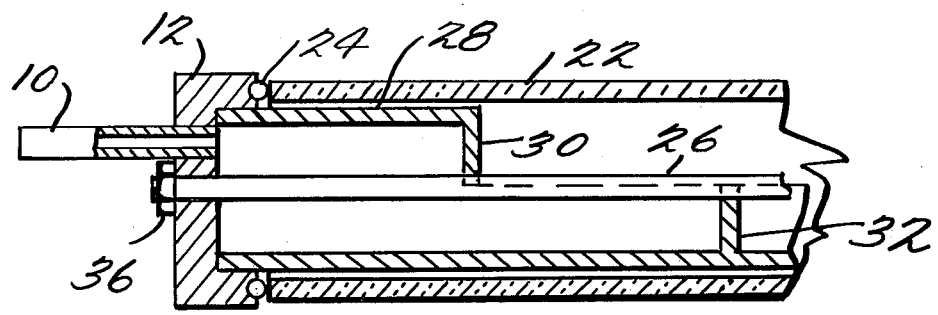
FIG. 3 is a detailed sectional side elevation, showing the details of the inlet end assembly of the device.

The metal and amalgam recovery device of the preferred form of this invention is designed for use in a dentist's office and receives the full flow of flushing fluid from the evacuation system, usually positioned adjacent a dentist's chair. When the doctor is drilling, pulling, cleaning and filling teeth, various kinds of debris must be removed from the mouth of a patient. Frequently, a flushing fluid is sprayed onto the work area inside the mouth to keep a tooth cool while it is being drilled and to wash away swarf and chips from the tooth and, in some cases, parts of the old filling being worked upon. At other times, tartar and buffing compounds are flushed from the mouth, small clots of blood may be washed away and parts of gauze or absorbent cotton packing elements may appear in the debris carried into the cuspidor by the vacuum-powered overflow outlet means which collects and removes the flushing fluid from the patient's mouth for delivery into the evacuation system. Also, the patient is asked to frequently rinse out his mouth and expectorate into the evacuation system to remove tooth chips, broken parts of old fillings and swarf from grinding operations.

The amalgam, in the form of particles or pieces of old fillings removed from the teeth, includes a precious metal component and as much as 40 to 60% mercury. Usually, larger pieces of fillings and parts of teeth are collected in the evacuation system itself, however, the grinding operations performed by a dentist produces a fine swarf that includes fine particles of amalgam and precious metals used for fillings in teeth. It is of significant value to recover these fine particles of gold and silver that usually form a part of these old fillings, but more importantly, the recovery of the mercury component of amalgam is of ecological value. The amalgam recovery device here shown is well adapted by reason of its proportions, for easy use in a dentist's office where normally as much as an ounce of fine particles of amalgam per week may be recovered. If the amalgam is 60% mercury, 0.6 oz. of mercury that would flow into a sewage system is thus recovered each week in a dentist's normal practice. The statistics indicate that there is an average of 1800 dentists per state in the U.S. alone. If all the amalgam from their activities were to be recovered, this would prevent approximately 2,808,000 ounces of mercury per year from entering sewage systems to, in most cases, wind up in our streams and rivers.

The amalgam recovery device of this invention makes use of a downwardly sloping, fully enclosed, through-flow chamber to receive all the flushing fluid and debris collected in the dental evacuation system. The entire drainage flow from the evacuation system, including the flushing fluid circulated in the evacuation system and the flushing fluid extracted from the patient's mouth, is delivered to the inlet passage to the device through nipple 10 formed on an inlet end cap 12 of the flow chamber 14. The trough-flow chamber includes the inlet cap that is preferably formed integral with a semi-circular trough element 16 that is supported at its inlet end on stainless steel legs 18 screwed into the body of the inlet end cap 12. The legs hold the inlet end lifted above the outlet end of the chamber that is supported on the bottom edge of the removable outlet end cap 20. A cylindrical glass housing 22 of a size to closely fit and telescope over the trough element is sealed to inlet cap 12 at the inlet end by an O ring seal 24. The opposite end of the glass housing may be assembled either permanently in a fixed relation with the outlet end cap 20 or may be separate therefrom and adapted to be sealed against the outlet cap with seal means similar to seal 24. The end cap 20 is provided with an outlet passage therethrough surrounded by a spout 26.

The trough element 16 is provided with a cylindrical inlet end portion 28 that receives the fluid flow entering through the inlet passage, which cylindrical portion defines an inlet chamber. A vertical baffle 30 located at the downstream end of the inlet chamber is formed integral with the cylindrical wall 28 to receive the thrust of the relatively high velocity infeed stream and direct the flow downwardly to cause the fluid and debris to flowthrough the semi-circular trough element 16. The remainder of the length of the semi-circular trough element downstream from baffle 30 is divided into a plurality of separate chambers by walls 32 to provide receptacles into which the particles of amalgam and precious metals settle as the flow of flushing fluid and debris passes through the device.

The cylindrical housing 22 has a diameter to neatly fit over the trough element 16 and is of a length to be just co-extensive therewith. The inlet cap 12 and outlet cap 20 together with the trough element are held assembled with the housing and caps fully enclosing the trough by means of the longitudinally extending stainless steel tie bolt 34. The bolt is drawn taut by nut means 36 to produce a fluid tight seal between the ends housing 22 and end caps 12 and 20.

When the unit is assembled as shown in FIG. 1, the desired flow of flushing fluid and debris is directed through the inlet passage to flow through the inlet chamber and impinge against baffle 30 to be directed downwardly into the multi-chambered inclined semi-circular trough element 16. The fluid flows from inlet chamber 28 and into and over the baffle means defining each chamber in the series of chambers defined by walls 32. Although the flushing fluid and debris may pass through the inlet passage at a relatively high velocity, the flow slows down as the diameter of the flow passage increases substantially when the stream moves into the enclosed inlet chamber and on down the inclined trough element. The trough is wholly enclosed so there can be no overflow of fluid that might otherwise produce unsanitary conditions. It is to be noted that within the enclosed flow passage the fluid flow is periodically agitated as it flows over baffles 32 disposed along the length of the trough. Usually, the fluid flow fills the entire internal volume between trough element 16 and the glass housing 22 and as the flow moves lengthwise through the flow passage thus formed the cross-sectional area of the passage changes to cause a slower flow velocity over the settlement chambers and a higher velocity flow in the space above walls 32. The amalgam and any precious metals can settle out of the stream in the quiter stream flow over the settlement chambers and the debris in the fluid is agitated as the flow passes into and flows through the flow passage that has the much smaller cross-sectional area over the walls 32. This speed-up of the flow agitates the debris floating in the stream to free the particles of amalgam and precious metals from the other debris present that might cause the heavier metal components to float, thus, the amalgam and metal particles are agitated free from other solids present in the fluid flow so that these particles deposit out of the flow when the stream velocity slows down while passing through the next following settlement chamber. Finally, after repeated agitation and quiescent flow conditions have been produced in the succeeding chambers, substantially all of the heavier metal particles will have fallen by gravity into the several deposition chambers, the fluid stream and remaining debris that floats in the flushing water will then pass out of the outlet passage 26 at outlet cap 36 to be delivered into the usual sewer outlet.

After the dentist has completed his daily work, the device may be disconnected from the evacuation system and first flushed out with clear water or even a disinfectant without washing away any of the amalgam or heavy precious metal particles collected in the deposit chambers of the trough element 16. When the assembly has been washed and disinfected, its contents can be inspected through the glass housing and, if need be, it can be disassembled by the simple operation of removing the nut 36 means 36 so that the outlet 26 may be removed and the glass housing 22 may be slid longitudinally off of the semi-circular trough 16. The deposited metal and amalgam particles can be recovered by dumping the trough and all of the parts can then be sterilized, if deemed advisable, before reassembly so that the most sanitary conditions can be easily maintained within the doctor's sphere of operations.

It is to be noted that the semi-circular shape of the trough 16 and cylindrical shape of housing 22 is of great practical value in minimizing the existence of crevices that might otherwise be difficult to clean and which would require more attention during a sterilization procedure.

The above-described device may be made of inert materials that have a long life and can be used with either a high pressure or a normal flushing fluid pumping means or even a vacuum source can be used for causing the desired flushing fluid flow through the device. The residual fluid flow existing from the device is delivered from the outlet passage 26 to the sewage system for ultimate disposal.

The fluid flow is directed into the device and the amalgam and precious metal particles are allowed to settle out of the flushing fluid stream as the flow continues through the semi-cylindrical trough. The size of the fluid flow passage is proportioned as above explained to cause suitable agitation and relative quiescent flow to take place throughout the length of the trough. Since the volume of flow is relatively small, a full size device for the purposes described above can be made dimensionally small so that it can be easily tucked away in an inconspicuous place between the evacuation system and sewer outlet. Because of its small size, it may be easily handled for recovery of the deposited metal material and cleaning operations.

The above-described preferred form of this invention is adpated for use in a dentist's office, but it is possible that modifications thereof for other purposes may occur to those skilled in the art that will fall within the following claims.

What is claimed is:

1. An amalgam recovery device for use in dental offices or the like for separating fine particles of precious metal and amalgam from debris carried in a flushing fluid comprising a downwardly sloping trough element having a floor; an inlet end cap at the upper end of said trough; said inlet cap having an inlet therethrough for the infeed into the trough of the flow of flushing fluid and debris from which the particles and amalgam are to be recovered; means to divide said trough into a plurality of compartments to receive the particles and amalgam depositing out of said flow; an outlet cap at the lower end of said trough having an outlet opening therethrough to pass the flushing fluid and any debris floating therein from the trough element after the particles and amalgam have been separated therefrom; a housing element situated between said end caps for enclosing said trough element; and means to hold said housing, caps and trough elements assembled in fluid tight relation whereby said device may be disassembled to be cleaned and sterilized and the particles and amalgam may be recovered from said compartments.

2. A device as in claim 1 wherein said trough and inlet cap are formed integral.

3. A device as in claim 1 wherein said trough element includes a cylindrical upper end portion integral with the remainder of the trough element with said remainder of the trough element being semi-circular to leave an open top over said baffles, and said housing is a cylindrical element into which said trough element telescopes.

4. A device as in claim 2 wherein said trough element takes the form of a semi-cylindrical floor and said housing is a cylindrical element into which said trough telescopes.

5. A device as in claim 4 wherein leg elements are fixed to said inlet cap to cause said trough to have said downward slope, said legs being formed of stainless steel and being removably attached to said cap.

6. A device as in claim 1 wherein said means to hold said housing, caps and trough elements assembled takes the form of a stainless steel tie rod extending lengthwise of the trough and through said end caps.

7. A device as in claim 5 wherein said means to hold said housing, caps and trough elements assembled takes the form of a stainless steel tie rod extending lengthwise of the trough and through said end caps.

8. A device as in claim 3 wherein said trough and inlet cap are formed integral.

9. A device as in claim 8 wherein leg elements are fixed to said inlet cap to cause said trough to have said downward slope, said legs being formed of stinless steel and being removably attached to said cap.

10. A device as in claim 8 wherein said means to hold said housing, caps and trough elements assembled takes the form of a stainless steel tie rod extending lengthwise of the trough and through said end caps.

11. An amalgam recovery device for use in dental offices for treating a flowing fluid stream to separate particles of precious metal and amalgam from debris carried in the flushing fluid used by the dentist in his activities comprising a downwardly sloping trough element haivng a semi-cylindrical floor and an integral cylindrical inlet end and cap, said inlet end cap having an inlet opening therethrough for the infeed into the trough of the flow of flushing fluid and debris from which the particles of metal and amalgam are to be recovered, the remainder of said trough element beyond the cylindrical inlet being semi-cylindrical and said remainder of the trough element having a plurality of separate compartments formed therein, said compartments being defined by spaced apart generally vertically disposed wall elements positioned crosswise of the semi-cylindrical remainder portion of the trough element, a baffle downstream of the inlet opening through the inlet cap to direct the incoming fluid stream to be treated downwardly onto the semi-cylindrical floor forming the remainder of said trough element, an outlet end cap at the lower end of said downwardly sloping trough element, said outlet end cap having an outlet passage therethrough to pass the treated stream of flushing fluid and the debris floating in the fluid from the trough element after the particles of metal and amalgam have been separated therefrom, a cylindrical glass housing releasably sealed against said inlet and outlet caps which housing together with said trough element forms a confined passage means for conveying said flushing fluid and debris over the compartments in said trough to permit the particles of metal and amalgam to deposit in said compartments while the remainder of the debris and flushing fluid flow outwardly through said outlet passage, and means to hold said housing and trough element assembled so that said housing may be released from said sealed engagement and removed from said trough element to permit the heavier particles of metal and amalgam to be recovered from said compartments of said trough element and so that the separated elements forming this device may be sterilized before reassembly.

* * * * *